United States Patent
Hsu et al.

(10) Patent No.: US 10,987,303 B2
(45) Date of Patent: Apr. 27, 2021

(54) EXTENDED RELEASE SUSPENSION FORMULATION OF LURASIDONE

(71) Applicant: LifeMax Laboratories, Inc., Redwood City, CA (US)

(72) Inventors: Chung-Chiang Hsu, Los Altos Hills, CA (US); Tzu-Ying Wu, Taipei (TW); Wei-Hsiang Wang, Taipei (TW); Chia-Yu Kuo, Taipei (TW)

(73) Assignee: LifeMax Laboratories, Inc., Redwood City, CA (US)

( * ) Notice: Subject to any disclaimer, the term of this patent is extended or adjusted under 35 U.S.C. 154(b) by 150 days.

(21) Appl. No.: 16/400,785

(22) Filed: May 1, 2019

(65) Prior Publication Data

US 2019/0336439 A1 Nov. 7, 2019

Related U.S. Application Data

(60) Provisional application No. 62/665,922, filed on May 2, 2018.

(51) Int. Cl.
| | |
|---|---|
| *A61K 9/00* | (2006.01) |
| *A61K 9/14* | (2006.01) |
| *A61M 5/32* | (2006.01) |
| *A61K 31/496* | (2006.01) |
| *A61K 47/40* | (2006.01) |
| *A61K 47/32* | (2006.01) |
| *A61K 47/26* | (2006.01) |
| *A61K 47/38* | (2006.01) |
| *A61K 47/10* | (2017.01) |

(52) U.S. Cl.
CPC .......... *A61K 9/0019* (2013.01); *A61K 31/496* (2013.01); *A61K 47/10* (2013.01); *A61K 47/26* (2013.01); *A61K 47/32* (2013.01); *A61K 47/38* (2013.01); *A61K 47/40* (2013.01); *A61M 5/329* (2013.01)

(58) Field of Classification Search
None
See application file for complete search history.

(56) References Cited

U.S. PATENT DOCUMENTS

| | | | |
|---|---|---|---|
| 5,002,940 A | 3/1991 | Geller et al. | |
| 8,283,352 B2 * | 10/2012 | Otoda | A61K 9/0095 514/254.02 |
| 2014/0348909 A1 | 11/2014 | Khera et al. | |
| 2015/0093442 A1 | 4/2015 | Kaneko et al. | |
| 2017/0196802 A1 * | 7/2017 | Ahmed | A61K 31/496 |
| 2017/0196855 A1 | 7/2017 | Ahmed et al. | |
| 2018/0338959 A1 * | 11/2018 | During | A61P 25/24 |
| 2019/0183896 A1 | 6/2019 | Sanders et al. | |

FOREIGN PATENT DOCUMENTS

WO  WO 2012/107890  8/2012

OTHER PUBLICATIONS

International Search Report and Written Opinion dated Aug. 28, 2019 for PCT/US2019/030235. 17 pages.

\* cited by examiner

*Primary Examiner* — Susan T Tran

(74) *Attorney, Agent, or Firm* — Sheppard Mullin Richter & Hampton LLP

(57) ABSTRACT

The present disclosure relates generally to depot formulations of lurasidone and methods of making depot formulations of lurasidone. The depot formulations include a suspending agent and are highly syringeable.

6 Claims, 2 Drawing Sheets

EXTENDED RELEASE SUSPENSION FORMULATION OF LURASIDONE

CROSS REFERENCE TO RELATED APPLICATIONS

This application claims the benefit under 35 U.S.C. § 119(e) of U.S. Provisional Application Ser. No. 62/665,922, filed May 2, 2018, the content of which is incorporated by reference in its entirety into the present disclosure.

BACKGROUND

Lurasidone hydrochloride is an atypical antipsychotic drug. It is used for treating schizophrenia and bipolar depression and is available as a tablet formulation for once daily, administration.

Depot formulations are desirable for providing a therapeutic dose of an active agent over an extended period of time, thereby providing convenience and improving patient compliance. There are several long acting injectable atypical antipsychotic products on the market. Long acting injectable product can be administered intramuscular once every week, once every month or once every three months. For depot formulations of anti-psychotic drugs, it is desirable to enable delivery of the depot formulation no more frequently than about once a month.

Depot formulations can be difficult to develop, in part, due to the high concentrations of drug required in order to provide therapeutic levels over an extended period of time. The problem is more difficult with active agents with low solubility such as lurasidone. Particle size is often critical to developing a depot formulation that will release the drug over the desired extended time period. In addition, a desirable depot formulation will be isotonic. Therefore, it is necessary to ensure particles do not agglomerate upon storage in an isotonic medium, thereby changing release characteristics. Hence, it can be challenging to develop a stable depot formulation that contains an optimal particle size and characteristics for consistent, extended drug release, and sufficient drug quantity.

Further, it is desirable for any injectable depot formulation to be administrable with small needle sizes, to minimize patient pain and improve compliance. Syringeability refers to the passability of a formulation through a syringe and can encompass the ease of withdrawing a formulation from a vial, and injectability of the formulation. Syringability is an important consideration in optimizing a depot formulation.

SUMMARY

The present invention provides a depot formulation of lurasidone or an acid salt thereof, and having a mean particle size of about 4 µm to about 100 µm, wherein the formulation comprises a suspending agent and is suitable for injection via a syringe needle having a gauge size of 20 gauge or smaller. The depot formulations of the invention are highly syringeable and, upon administration, can deliver a therapeutic dose of lurasidone for at least about 28 days.

In one embodiment, the concentration of lurasidone crystals in the composition is greater than about 250 mg/ml and the vehicle comprises a suspending agent and a buffer, and wherein the suspending agent is in an amount from about 0.1% (w/w) to about 7.5% (w/w).

In some embodiments, the mean particle size is between 10 µm and 40 µm, and preferably about 20 µm.

In some embodiments the formulation is suitable for injection via a syringe needle having a gauge size of 22 gauge or smaller, or preferably, having a gauge size of 24 gauge or smaller.

In some embodiments, lurasidone crystals in the formulation is lurasidone base, and the amount of lurasidone crystals in the formulation is greater than about 280 mg/mL, or greater than about 300 mg/mL.

In some embodiments, the suspending agent is selected from the group consisting of polyethylene glycol, carboxymethylcellulose sodium, methylcellulose, polyvinyl pyrrolidone, dextrin, medium-chain triglycerides, sucrose, hydroxypropyl methyl cellulose, chistosan, polyoxyethylene, polyoxy-propylene ethers, polyvinyl alcohol, hydroxypropyl betacyclodextrin, gelatin, sucrose, and combinations thereof. Preferably, the suspending agent is selected from the group consisting of polyethylene glycol, carboxymethylcellulose sodium, methylcellulose, polyvinyl pyrrolidone, and combinations thereof. In some embodiments, the composition comprises from about 0.1% (w/w) to about 7.5% of the suspending agent. In further embodiments, the suspending agent is in an amount from about 0.1% (w/w) to about 6% (w/w), from about 0.2% (w/w) to about 6% (w/w), from about 0.5% (w/w) to about 6% (w/w), from about 1% (w/w) to about 6% (w/w).

The formulations of the invention do not require the use of surfactants in order to obtain good syringability. Optionally, a surfactant may be included in the formulation. In some embodiments, the surfactant is selected from the group consisting of polysorbate 80, polysorbate 20, sorbitan ester, polyoxyethylene hydrogenated castor oil 50, polyoxyethylene hydrogenated oil castor oil 60, poloxamer 188, polyoxyethylene castor oil, and combinations thereof. Preferably, the formulation includes a surfactant selected from the group consisting of polysorbate 20, polysorbate 80, sorbitan monolaurate 20, and poloxamer 188. In embodiments comprising a surfactant, the surfactant may be present in an amount from about 0.2% (w/w) to about 2.0% (w/w).

The formulation will be isotonic and will include a buffer. The buffer may be selected from the group consisting of sodium dihydrogenphosphate, disodium hydrogenphosphate, sodium phosphate, potassium dihydrogenphosphate, dipotassium hydrogenphosphate, citric acid, sodium hydroxide, hydrochloric acid or the combinations thereof.

Also provided are methods of treating patients with schizophrenia or bipolar depression by administration of the depot formulations of the invention via intramuscular injection.

Also provided are methods of making depot formulations of the inventions by a wet milling process. The method includes pre-mixing lurasidone crystals in a milling medium comprising a suspending agent and a buffer, wet-milling the suspension, wet-screening the resulting suspension, collecting particles having sizes from about 10 µm to about 40 µm, adjusting the concentration by addition or removal of milling medium to a concentration of lurasidone of about 250 mg/ml to about 400 mg/ml. Additional suspending agent may be added after wet-screening to a final concentration of about 0.1% (w/w) to about 7.5% (w/w). Preferably, wet milling is performed using a ball grinder.

Also provided, in some embodiments, are products prepared by the preparation methods disclosed herein. In some embodiments, the product further comprises a surfactant. Non-limiting examples of surfactants include polysorbate 20, polysorbate 80, sorbitan monolaurate 20, and poloxamer 188. Non-limiting examples of suspending agents include polyethylene glycol, carboxymethylcellulose sodium, methylcellulose, polyvinyl pyrrolidone, and combinations thereof.

Figure 1:
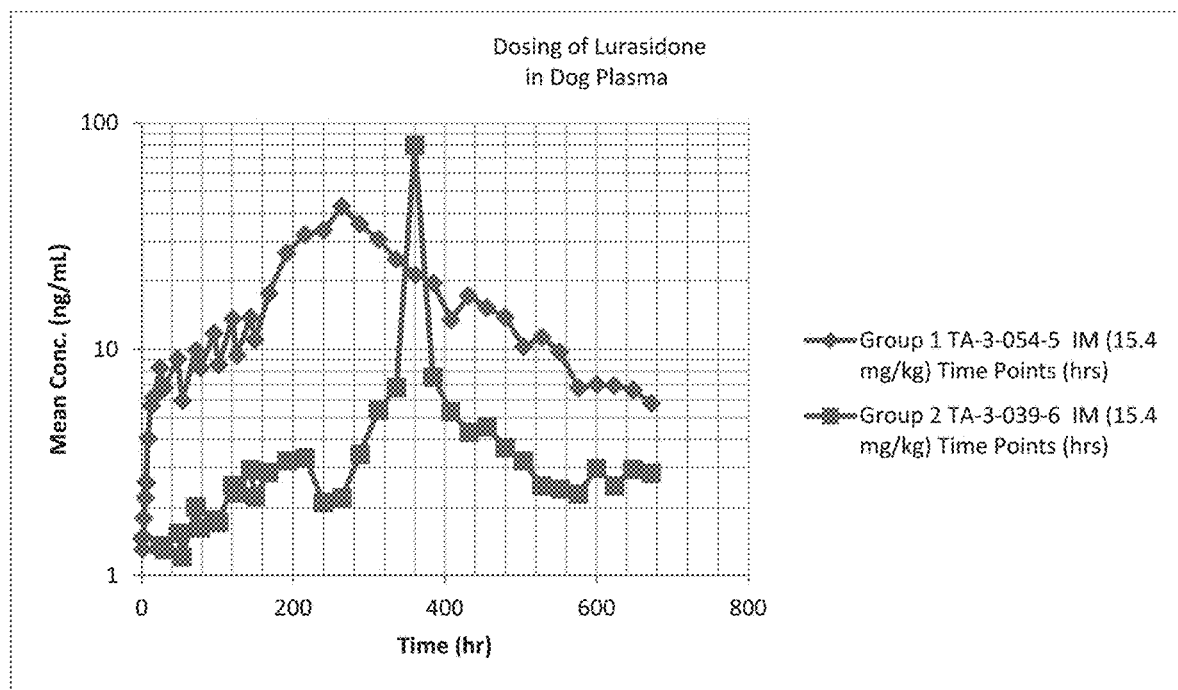
FIG. 1 shows the results of a pharmacokinetic study of lurasidone dosing in dogs.

It will be recognized that some or all of the figures are schematic representations for purpose of illustration.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

Extended Release Suspension Formulations

Lurasidone has a chemical name of (3aR,4S,7R,7aS)-2-{(1R,2R)-2-[4-(1,2-benzisothiazol-3-yl)piperazin-1-ylmethyl] cyclohexylmethyl}hexahydro-4,7-methano-2H-isoindole-1,3-dione, with a structure of

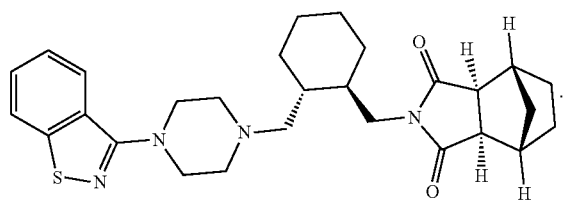 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

Lurasidone can be prepared and used as an acid salt, which is a salt with an inorganic acid or an organic acid. Non-limiting examples of inorganic acids include hydrochloric acid, hydrobromic acid, hydroiodic acid, and sulfuric acid. Non-limiting examples of organic acids includes phosphoric acid, acetic acid, oxalic acid, citric acid, malic acid, tartaric acid, maleic acid, and fumaric acid. A specific example is a salt of hydrochloride.

Excipients used to optimize stability (e.g., reduce sedimentation) of optimal particle-size formulations often lead to formulations with poor syringeability. Further, to avoid injection more than, e.g., once a month, or the need of multiple-site injections for high-dose patients, it is desirable to develop an injectable formula with high drug concentrations, e.g., about 280 mg/mL or more. Moreover, for the comfort of the patients, it is desirable to use thinner needles (needles with higher gauge numbers, e.g., 20 gauge or higher). However, both the high concentrations and the smaller needles present greater challenges to syringeability, and therefore present challenges to developing a practical depot formulation that is able to provide a therapeutic dose of active agent for 28 days or more while enabling a small needle size to minimize patient discomfort.

U.S. Pat. No. 9,469,630 discloses injectable suspensions of lurasidone crystals of different particles size. Example 15 in the 9,469,630 patent concludes that, in order to achieve acceptable needle passability for 22-gauge needles at a 400 mg/mL drug concentration, the particle size needed to be less than 15.2 µm (see, col. 47, lines 1-4 and Table 27). Further, to prepare such a formulation, a specific nonionic surfactant is required (see, e.g., col. 3, lines 9-19).

It is a surprising and unexpected discovery of the present disclosure that, with an improved preparation process and the addition of a suspending agent, a depot formulation of lurasidone crystals having a concentration of about 300 mg/mL and mean particle size of 16.2 µm can be prepared which have good passability through 22-gauge or even 23-gauge needles. Even further surprisingly, such suspension formulations do not require the addition of a surfactant.

The same improvement in preparation process and formulation also led to stable formulations with greatly improved syringeability of high lurasidone concentrations such that the resulting depot formulations are capable of providing therapeutic quantities of lurasidone over at least a 28-day period, even for patients requiring the highest doses. Each of these improvements would have been entirely unexpected based on the conventional knowledge in the art as exemplified in U.S. Pat. No. 9,469,630.

The present disclosure provides a depot formulation of lurasidone comprising crystals suspended in a pharmaceutically acceptable vehicle. The crystals include lurasidone or an acid salt thereof and have a mean particle size of about 10 plm to about 40 µm, wherein the amount of crystals in the composition is greater than about 250 mg/mL and the vehicle comprises a suspending agent from about 0.1% (w/w) to about 7.5% (w/w). The formulations of the invention do not require a surfactant, but a surfactant may optionally be included.

The term "suspending agent" as used herein refers to a pharmaceutical acceptable excipient that promotes particle suspension or dispersion and reduces sedimentation. Suspending agents retard settling and agglomeration of particles by functioning as an energy barrier, which minimizes interparticle attraction. Suspending agents include protective colloids and viscosity-inducing agents. Protective colloids differ from surfactants in that they do not reduce interfacial tension. Many agents that are protective colloids in low concentration (<0.1%) are viscosity builders in higher concentrations (>0.1%). See G. Jain, R. K. Khar, F. J. Ahmad, *Theory and Practice of Physical Pharmacy*, 2011. The increase in viscosity of the solution is helpful to prevent sedimentation of the suspended particles. A suspension has well developed thixotropy. At rest the solution is sufficient viscous to prevent sedimentation and thus aggregation or caking of the particles. When agitation is applied the viscosity is reduced and provide good flow characteristic.

Examples of suspending agents include polysaccharides, inorganic salts, and polymers. Specific examples of suspending agents include, without limitation, alginates, methylcellulose, hydroxyethylcellulose, carboxymethylcellulose, colloidal silicon dioxide, agar, calcium stearate, hypromellose, magnesium aluminum silicate, guar gum, carboxymethylcellulose sodium, microcrystalline cellulose, acacia, tragacanth, xanthan gum, bentonite, carbomer, carageenan, powdered cellulose, gelatin, polyethylene glycol, povidone, dextrin, medium-chain triglycerides, sucrose, hydroxypropyl methyl cellulose, chistosan, polyoxyethylene, polyoxypropylene ethers and combinations thereof. See Handbook of pharmaceutical excipients, $6^{th}$, Raymond C Rowe, Paul J Sheskey and Marian E Quinn 2009.

In a preferred embodiment, the suspending agent is selected from polyethylene glycol (e.g., polyethylene glycol 4000), carboxymethylcellulose sodium, methylcellulose, povidone, and combinations thereof. In one embodiment, the suspending agent is polyethylene glycol 4000. In another embodiment, the suspending agent is carboxymethylcellulose sodium.

The concentration of the suspending agent can generally be from about 0.1 mg/mL to about 200 mg/mL, or from about 0.5 mg/mL to about 100 mg/mL, from about 1 mg/mL to about 75 mg/mL, from about 5 mg/mL to about 60 mg/mL, from about 5 mg/mL to about 20 mg/mL, or from about 40 mg/mL to about 60 mg/mL. In some embodiments, concentration of the suspending agent is from about 0.1% (w/w) to about 7.5% (w/w), or from about 0.1% (w/w) to about 6% (w/w), from about 0.2% (w/w) to about 6% (w/w), from about 0.5% (w/w) to about 6% (w/w), from about 1% (w/w) to about 6% (w/w).

For polyethylene glycol 4000, the concentration can be from about 10 mg/mL to about 100 mg/mL, from about 25 mg/mL to about 75 mg/mL, from about 40 mg/mL to about 70 mg/mL, or from about 50 mg/mL to about 60 mg/mL. For carboxymethylcellulose sodium, the concentration can be from about 1 mg/mL to about 50 mg/mL, from about 2 mg/mL to about 30 mg/mL, from about 5 mg/mL to about 20 mg/mL, or from about 7 mg/mL to about 15 mg/mL. For methylcellulose, the concentration can be from about 0.1 mg/mL to about 10 mg/mL, from about 0.2 mg/mL to about 5 mg/mL, from about 0.5 mg/mL to about 2 mg/mL, or from about 0.75 mg/mL to about 1.25 mg/mL. For polyethylene glycol 4000, the concentration can be from about 1% (w/w) to about 10% (w/w), from about 2.5% (w/w) to about 7.5% (w/w), from about 4% (w/w) to about 7% (w/w), or from about 5% (w/w) to about 6% (w/w). For carboxymethylcellulose sodium, the concentration can be from about 0.1% (w/w) to about 5% (w/w), from about 0.2% (w/w) to about 3% (w/w), from about 0.5% (w/w) to about 2% (w/w) or from about 0.7% (w/w) to about 1.5% (w/w). For methylcellulose, the concentration can be from about 0.01% (w/w) to about 1% (w/w), from about 0.02% (w/w) to about 0.5% (w/w), from about 0.05% (w/w) to about 0.2% (w/w), or from about 0.075% (w/w) to about 0.125% (w/w).

The term "surfactant" as used herein means agents that lower the surface tension (or interfacial tension) between two liquids or between a liquid and a solid. Surfactants are usually organic compounds that are amphiphilic, i.e., they contain both hydrophobic groups (tails) and hydrophilic groups (heads). Therefore, a surfactant contains both a water-insoluble (or oil-soluble) component and a water-soluble component.

Surfactants can be classified according to polar head group. A non-ionic surfactant has no charged groups in its head. Nonionic surfactants have covalently bonded oxygen-containing hydrophilic groups, which are bonded to hydrophobic parent structures. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic.

In one embodiment, the composition does not contain any surfactant, or does not contain more than a trace amount of surfactant (e.g., <5 mg/mL, <1 mg/mL, <0.1 mg/mL, <0.01 mg/mL, or <0.001 mg/mL). In one embodiment, the composition does not contain any nonionic surfactant, or does not contain more than a trace amount of nonionic surfactant (e.g., <5 mg/mL, <1 mg/mL, <0.1 mg/mL, <0.01 mg/mL, or <0.001 mg/mL). In one embodiment, the composition does not contain any zwitterionic surfactant, or does not contain more than a trace amount of zwitterionic surfactant (e.g., <5 mg/mL, <1 mg/mL, <0.1 mg/mL, <0.01 mg/mL, or <0.001 mg/mL).

In one embodiment, the composition does not contain any of polysorbate, polyoxyethylene hydrogenated castor oil, poloxamer or polyoxyethylene castor oil. In one embodiment, the composition does not contain more than 5 mg/mL, 2 mg/mL, 1 mg/mL, 0.5 mg/mL, 0.1 mg/mL, 0.01 mg/mL, or 0.001 mg/mL of polysorbate, polyoxyethylene hydrogenated castor oil, poloxamer or polyoxyethylene castor oil, collectively.

In the presence of a suspending agent, in some formulations, the addition of a surfactant can further enhance the syringeability of the formulation. In one embodiment, provided is a composition comprising crystals of lurasidone or an acid salt thereof having a mean particle size of about 10 µm to about 40 µm and a surfactant. The surfactant can be a non-ionic surfactant, an ionic surfactant (anionic or cationic), or a zwitterionic surfactant. Examples of surfactants include polysorbate (such as polysorbate 80 and polysorbate 20), sorbitan ester, polyoxyethylene hydrogenated castor oil (such as polyoxyethylene hydrogenated castor oil 50 and polyoxyethylene hydrogenated oil castor oil 60), poloxamer 188 or polyoxyethylene castor oil.

Preferred surfactants include polysorbate 20, polysorbate 80, sorbitan monolaurate 20, and poloxamer 188. In one embodiment, the surfactant is polysorbate, such as polysorbate 20 or polysorbate 80. The concentration of surfactant can be from about 1 mg/mL to about 50 mg/mL, from about 2 mg/mL to about 30 mg/mL, from about 5 mg/mL to about 20 mg/mL, or from about 7 mg/mL to about 15 mg/mL. In preferred embodiments, the surfactant is present in an amount of about 0.2% to about 2%. In embodiments where the surfactant is polysorbate 20, it is present in an amount of from about 0.2% to about 2%, and with certain suspending agents, it is present in an amount from about 1% to about 2%, preferably around 1%.

The presently disclosed formulations have good syringeability. Syringeability can be determined, for instance, by injecting an amount of the formulation (e.g., 1 mL) through a needle (e.g., 18-25 gauge) into a test animal tissue (pork ham). The syringeability can be measured by the time and/or pressure required to inject the formulation. A formulation with a desired level of syringeability can be injected through a relatively thin needle at a relatively fast speed (to reduce pain and stress).

The particle size of lurasidone crystals is an important factor in controlling the in vivo release rate from a depot formulation. In order to provide a depot formulation providing extended release of lurasidone over at least about a 28-day period, the mean particle size should be from about 10 μm to about 40 μm. In some embodiments, the mean particle size of the crystals of lurasidone or an acid salt thereof is from about 15 μm to about 30 μm, preferably about 20 μm. In some embodiments, the mean particle size of the crystals of lurasidone or an acid salt thereof is at least about 16 μm, 17 μm, 18 μm, 19 μm, or 20 μm.

In some embodiments, the composition contains at least 220 mg/mL the crystals of lurasidone or an acid salt thereof. In some embodiments, the concentration is at least 230 mg/mL, 240 mg/mL, 250 mg/mL, 260 mg/mL, 270 mg/mL, 280 mg/mL, 290 mg/mL, 300 mg/mL, 310 mg/mL, 320 mg/mL, 330 mg/mL, 340 mg/mL, 350 mg/mL, 360 mg/mL, 370 mg/mL, 380 mg/mL, 390 mg/mL, 400 mg/mL, 410 mg/mL, or 420 mg/mL of the crystals. Preferably, the concentration is equal to or greater than 280 mg/ml.

In order to provide a depot formulation that will provide therapeutic levels of lurasidone release over at least a 28-day period even for high dose patients, it is important for the formulation to contain sufficient drug while maintaining stability and syringeability. In another surprising and unexpected discovery, with an improved preparation process and the addition of a suspending agent (with or without a surfactant), a suspension of lurasidone crystals with suitable syringeability can be prepared that contains lurasidone crystals of from about 10 um to about 40 um, and a concentration of from about 250 mg/ML to about 400 mg/ml of the crystals. Preferably, depot formulations of the invention contain at least about 280 mg/ml of lurasidone crystals.

The depot formulation will also include a buffer, and may be isotonic. Examples of buffer include, without limitation, sodium dihydrogenphosphate, disodium hydrogenphosphate, sodium phosphate, potassium dihydrogenphosphate, dipotassium hydrogenphosphate, citric acid, sodium hydroxide, hydrochloric acid or the combinations thereof. In an isotonic formulation, the lurasidone is preferably lurasidone base to reduce particle agglomeration.

In depot formulations of the invention without surfactant, the preferred suspending agent is polyvinyl pyrrolidone K17. In these embodiments, the polyvinyl pyrrolidone may be between about 0.5% (w/w) and 1.0% (w/w). In depot formulations of the invention containing polysorbate 20 as the surfactant, it is preferably used at concentrations from about 0.2% (w/w) to about 2.0% (w/w), and in some case in concentrations from about 1% (w/w) to about 2% (w/w), from about from about 0.2% (w/w) to about 1.5% (w/w), from about 0.2% (w/w) to about 1.0% (w/w), from about from about 0.5% (w/w) to about 1.5% (w/w), or from about from about 0.5% (w/w) to about 1% (w/w). In depot formulations of the invention comprising poloxamer 188 as the surfactant, it is preferably used at a concentration of from about 0.1% (w/w) to about 1% (w/w). In a preferred embodiment, the suspending agent is PEG 4000 at about 5% (w/w), the surfactant is polysorbate 20 at about 1% (w/w) to about 2%, in a phosphate buffer (0.6% sodium dihydrogen phosphate monohydrate and 0.112% sodium hydroxide aqueous solution) with lurasidone base crystals with a mean particle size of about 20 μm.

For convenience of care providers, the formulation can be provided in a kit or package that includes a container enclosing the formulation. The container may be part of a syringe or separate from the syringe. The kit or package also includes a needle that can be suitably mounted to the syringe. The size of the needle, in some embodiments, is equal to or smaller than 18G, 19G, 20G, 21G, 22G, 23G, 24G, or 25G. In one embodiment, the needle has a size that is 20G or smaller. In one embodiment, the needle has a size that is 21G or smaller. In one embodiment, the needle has a size that is 22G or smaller. In one embodiment, the needle has a size that is 23G or smaller.

Also provided, are methods of treating a patient suffering from a psychotic disease or condition, such as schizophrenia or bipolar depression by intramuscular injection of the depot formulations of the present invention.

Preparation of the Formulations

The present disclosure provides a process for preparing crystal particles of lurasidone or an acid salt for use in preparing suspension formulations. The method includes milling (wet milling) crystals of lurasidone or the acid salt thereof in a milling medium comprising a suspending agent and water, screening the milled crystals, and collecting crystals having sizes as needed and adjusting to final desired concentrations.

Step 1: Wet Milling

To decrease particle sizes of lurasidone (or lurasidone acid salt form) crystals and to avoid particle aggregation during particle size reduction, it is preferred by means of premixing with liquid medium and wet milling. For example, lurasidone crystals are premixed with a milling medium and wet milled to the desired mean particle size. Suitable wet milling processes are known in the art and include ball mills (or bead mills), and rotor-stator homogenizers. Different materials may be used for the grinding media. The beads, or balls, can be made of plastic, glass, ceramics such as aluminum oxide and zirconium oxide, steel, and tungsten carbide. Factors that influence the ultimate particle size are the size of the grinding media, the time the material spends in the grinding chamber, the number of passes through the mill, and the speed of agitation For instance, a planetary ball miller (model: Planetary Ball Mill PM 100, Retsch) can be used. The milling medium can include suspending agent, optionally a buffer solution, optionally a surfactant, optionally an isotonic agent, optionally an antioxidant and water for injection. For example, the milling medium may include surfactant or polyvinyl pyrrolidone K17 with no surfactant, in each case in a phosphate buffer. Milling may be done in ajar with balls, with the material of each being ZrO2, and a jar size of 50 ml. With starting particle size of Dv 40 um, to obtain mean particle size of about 20 um, the following conditions may be used: ball size: 10 mm; number of balls: 10; revolution speed: 250 rpm; grinding time: 20 min (interval: 2 min, rest: 3 min).

Step 2: Wet Screening

Obtaining target particle sizes of lurasidone (or lurasidone acid salt form) by wet screening with standard sieves and washing with screening medium, which is preferably the same as the milling medium. The method also can include determining the particle size distribution of lurasidone (or lurasidone acid salt form) after screening with a laser diffraction particle size analyzer (model: Mastersizer 3000, Malvern Instruments) by wet method using water and surfactant as a dispersion medium. The sample is collected from the sieve pan following wet screening with a 63 μm sieve to obtain particles with a mean particle size of about 20 μm.

Step 3: Adjusting to Needed Concentration

Suspension is collected after sieving wet screening in a container and adjust concentration of active ingredient to 300 mg/mL to 400 mg/mL by adding or removing the supernatant volume after crystals are completely precipitated. This is performed by determining the original concentration of the suspension by HPLC, then allowing the suspension to precipitate. The concentration is then adjusted by removing or adding supernatant with pipet to the desired concentration. Final concentration is confirmed by HPLC. The sample for determining concentration is taken by agitating the suspension with a stirring machine (model: NZ-1200, EYELA) and the concentration is determined by high performance liquid chromatography (model: Agilent 1260 II Infinity LC).

Step 4: Add Suspending Agent and/or Surfactant for Formulation

Depending on the suspending agent in the milling medium, suspending agent may be added (with or without surfactant) into the suspension, and the resulting mixture stirred thoroughly until a uniform suspension is obtained.

Suspending agent preferably comprises at least one of polyethylene glycol 4000, polyvinylpyrrolidone (PVP), carboxymethylcellulose sodium, methylcellulose, and surfactant comprises at least one of polysorbates, e.g. polysorbate 20, polysorbate 80.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Preparation of Crystal Particles

The examples describe a process for preparing crystal particles of lurasidone and suspension formulations.

Step 1: Wet Milling

To decrease particle sizes of lurasidone hydrochloride crystals and to avoid particle aggregation during particle size reduction, this example employed a method that premixed the crystals with liquid medium and wet milling. Planetary ball miller (model: Planetary Ball Mill PM 100, Retsch) was used. The grinding medium included a suspending agent, optionally with a buffer solution, a surfactant, an isotonic agent, antioxidant and water.

Step 2: Wet Screening

Wet screening with standard sieves and washing with screening medium by using the same milling medium. The particle size distribution of lurasidone was determined after screening with a laser diffraction particle size analyzer (model: Mastersizer 3000, Malvern Instruments) by wet method using water and surfactant as a dispersion medium.

Step 3: Adjusting to Needed Concentration

Suspensions were collected after sieving wet screening in a container and concentration of active ingredient was adjust to 300 mg/mL to 400 mg/mL by adding or removing the supernatant volume after crystals were completely precipitated. High concentrations of lurasidone were used in the examples that follow in order to challenge syringeability and/or resuspension times of resulting formulations. The sample for determining concentration was taken by agitating the suspension with a stirring machine (model: NZ-1200, EYELA) and the concentration was determined by high performance liquid chromatography (model: Agilent 1260 II Infinity LC).

Step 4: Add Suspending Agent and/or Surfactant for Formulation

Depending on the suspending agent in the milling medium, additional suspending agent (with or without surfactant) may be added into the suspension, which is then stirred thoroughly until a uniform suspension is obtained. The suspending agent used included polyethylene glycol 4000, polyvinylpyrrolidone (PVP), carboxymethylcellulose sodium, methylcellulose. The surfactant used included polysorbates, e.g. polysorbate 20, polysorbate 80.

Example 2

According to the processes as described in Example 1, the milling medium was prepared with polyvinylpyrrolidone K17 and buffer solution included sodium dihydrogen phosphate monohydrate, sodium hydroxide and water for injection as shown in Table 1.

TABLE 1

| Wet Milling and Premix Medium | | |
|---|---|---|
| polyvinylpyrrolidone K 17 | 0.7% (w/v) | 7 mg/mL |
| sodium dihydrogen phosphate monohydrate | 0.6% (w/v) | 6 mg/mL |
| sodium hydroxide | 0.112% (w/v) | 1.12 mg/mL |
| water for injection | | 1 mL (total volume) |

The particles sizes were milled to get a relatively large particle size distribution via wet milling, the starting material of lurasidone crystals had particle size of Dv50 around 40 μm. The ball milling apparatus included planetary ball mill (model: Planetary Ball Mill PM 100, Retsch), milling jar and milling balls. Zirconium oxide (ZrO2) was selected as material of the milling jar and milling balls.

Lurasidone crystals, milling ball and milling medium were introduced into a milling jar and each had one third volume respectively. The revolution speed was 100 rpm and grinding interval time is 2 minutes with 3 minutes rest time for 2 cycles.

Particle size was separated by wet screening the suspension after wet milling on stacked standard sieves; the mesh size order of sieves from top to bottom were 100 μm, 63 μm, 45 μm and 20 μm. The suspension was washed by wet screening medium, the same as wet milling medium, with high flow rate in order to achieve complete screening and obtain narrow particle size distribution of particles on each layer.

The particles were collected on each sieve separately into sterilized containers by rinsing with milling medium and pipetting the suspension up gently with dropper to avoid breaking the fragile particles, and stood for particle precipitation. The concentrations of the suspensions were determined and adjusted to target concentration by adding or removing supernatant amount.

Example 3

For the purpose of preliminarily evaluating the effect of vehicle composition on syringeability, the formulations with or without suspending agent (e.g. polyethylene glycol 4000) and surfactant (one of the ingredients of polysorbate 20, polysorbate 80 and sorbitan monolaurate) were tested. The formulations had active ingredient concentration in the range of 280 to 320 mg/mL with the mean particle size of 38.65 μm crystals.

For each formulation, 1 mL of each suspension was transferred into a 2.5 mL syringe mounted with 18-gauge, 1½ needle. To evaluate the syringeability, pork ham (hind leg pork) was selected to mimic the injection into human muscle. In Table 2, "O" means the entire amount of suspension could be injected into the pork ham. "X" means the suspension was unable to be injected partially or entirely into the pork ham. As shown in Table 2, the syringeability was poor when only using povidone and/or surfactant in the formulation. However, polyethylene glycol 4000 improved syringeability with or without surfactant. In addition, the formulation combined with suspending agent and surfactant prevented bubbles generated during mixing which happened while formulation comprises only polyethylene glycol 4000 and without surfactant.

TABLE 2

| Mean particle size (µm) (span) | Concentration of active ingredient (mg/mL) | Additive | Additive concentration (mg/mL) | Syringeability |
|---|---|---|---|---|
| 38.65 (1.20) | 280~320 | None | | X |
| | | polyethylene glycol 4000 | 56 mg/mL | O |
| | | polysorbate 20 | 2 mg/mL | X |
| | | polysorbate 80 | 2 mg/mL | X |
| | | sorbitan monolaurate 20 | 2 mg/mL | X |
| | | polyethylene glycol 4000 polysorbate 20 | 50 mg/mL 3 mg/mL | O |
| | | polyethylene glycol 4000 polysorbate 80 | 50 mg/mL 2 mg/mL | O |

Example 4

To further investigate what kind of suspending agent can improve syringeability, the pork ham injection test was also applied on the formulations with different suspending agents, each contained one of the ingredients of polyethylene glycol 4000, carboxymethylcellulose sodium and methylcellulose. The active ingredient concentration was in the range of 280 to 310 mg/mL and had larger particle size which mean particle size was 54.1 µm. Table 3 shows the syringeability results; all of the three suspending agents improved syringeability compared with the suspension without any of these three suspending agents.

TABLE 3

| Mean particle size (µm) (span) | Concentration of active ingredient (mg/mL) | Additive | Additive concentration (mg/mL) | Syringeability |
|---|---|---|---|---|
| 54.1 (1.23) | 280~310 | None | | X |
| | | polyethylene glycol 4000 | 56 mg/mL | O |
| | | carboxymethylcellulose sodium | 10 mg/mL | O |
| | | methylcellulose | 1 mg/mL | O |
| | | polyethylene glycol 4000 polysorbate 20 | 56 mg/mL 10 mg/mL | O |

Example 5

In order to further evaluate the combination effect of suspending agents and surfactants on improving syringeability, the suspensions with larger mean particle size crystals leading to poor syringeability were used. Table 4 illustrates that the formulation participated with suspending agent chosen from one of polyethylene glycol 4000, carboxymethylcellulose sodium or methylcellulose and without surfactant cannot be injected into pork ham while the active ingredient concentration is in the range of 280 to 310 mg/mL and mean particle size is 78.2 μm. On the other hand, the addition of polysorbate 20 into the formulation with the either polyethylene glycol 4000 or carboxymethylcellulose sodium as the suspending agent, the syringeability was significantly improved.

TABLE 4

| Mean particle size (um) (span) | Concentration of active ingredient (mg/mL) | Additive | Additive concentration (mg/mL) | Syringeability |
|---|---|---|---|---|
| 78.2 (1.22) | 280~310 | None | — | X |
| | | polyethylene glycol 4000 | 56 mg/mL | X |
| | | carboxymethylcellulose sodium | 10 mg/mL | X |
| | | methylcellulose | 1 mg/mL | X |
| | | polyethylene glycol 4000 polysorbate 20 | 56 mg/mL 10 mg/mL | ○ |
| | | carboxymethylcellulose sodium polysorbate 20 | 10 mg/mL 10 mg/mL | ○ |
| | | methylcellulose polysorbate 20 | 1 mg/mL 10 mg/mL | X |

Example 6

To reduce the possibility of injecting in more than 1 site for high-dose patient, it is beneficial to develop an injectable formula with high drug concentration. Therefore, syringeability study of the suspension with high drug concentration and different gauge sizes, including 18, 20, 22, 23 and 25 gauges, were conducted. The passability limits of needle gauge size for each formulation are shown in Table 5.

TABLE 5

| Mean particle size (um)/(span) | Concentration of active ingredient (mg/mL) | Additive Type | Additive | Additive concentration (mg/mL) | Largest passable gauge size |
|---|---|---|---|---|---|
| 16.2 (2.21) | 385~415 | | None | — | 20G |
| | | suspending agent | polyethylene glycol 4000 | 56 | 22G |
| | | | carboxymethylcellulose sodium | 10 | 23G |
| | | | methylcellulose | 1 | 20G |
| | | surfactant | polysorbate 20 | 10 | 23G |
| | | combination | polyethylene glycol 4000 polysorbate 20 | 56 10 | 25G |
| | | | carboxymethylcellulose sodium polysorbate 20 | 10 10 | 25G |
| | | | methylcellulose polysorbate 20 | 1 10 | 25G |

The results show that either suspending agent or surfactant alone can improve the syringeability when the passability limit is gauge size from 20 gauge to 23 gauge. However, the formulation containing both suspending agent and surfactant can push the syringeability limit of gauge size to 25 gauge at the same concentration.

Example 7

To evaluate in vivo performance, two pharmacokinetic studies in dogs were performed. Two formulations were compared in each study, and were administered by intramuscular injection to four animals each at 15.4 mg/kg. Formulation compositions are shown below. Before filling the syringe, the formulations were shaken vigorously for at least one minute to prepare a homogeneous suspension. The syringe was filled and again shaken vigorously for at least 30 seconds, and then the injection was performed immediately. In each case, 23-gauge needles were used for delivery. Blood samples were collected at: pre-dose, and hours 0.5, 1, 2, 3, 4, 5, 6, 8, 12, 16, 24, 30, 48, 54, 72, 78, 96, 102, 120, 126, 144, 150, and 168, then Q24 hours until Day 28 following dose administration.
Formulation Composition of $1^{st}$ Dog PK Study:
Vehicle Composition:

| Excipient | Function | Amount (mg/mL) |
|---|---|---|
| polysorbate 20 | wetting agent | 10 |
| polyethylene glycol 4000 | suspending agent | 50 |
| citric acid | chelating agent (inhibit the oxidation of PEG) | 6.857 |
| sodium dihydrogen phosphate monohydrate ($NaH_2PO_4$—$H_2O$) | buffer | 6 |
| sodium hydroxide (NaOH) | | 5.4 |
| water (purified water) | | vol. to 1 mL |

API concentrations in the medium were 298 mg/mL for group 1 and group 2. The mean lurasidone particle size for group 1 was 4.97 μm, and for group 2 was 40.5 μm.
Formulation Composition of $2^{nd}$ Dog PK Study:
Vehicle Composition:

| Excipient | Function | Amount (mg/mL) |
|---|---|---|
| PVP K17 | suspending agent | 6.32 |
| carboxymethycellulose sodium | suspending agent | 10 |
| citric acid | buffer | 9.15 |
| sodium dihydrogen phosphate monohydrate ($NaH_2PO_4$—$H_2O$) | | 8.26 |
| sodium hydroxide (NaOH) | | 7.79 |
| water (purified water) | | vol. to 1 mL |

API concentrations in the medium were 292 mg/mL for group 1 and 295 mg/mL for group 2. The mean lurasidone particle size for group 1 was 19.7 μm and for group 2 was 10.5 μm.

Results of Study 1 are shown below and in FIG. 1.
Group 1 (TA-3-054-5):

| Animal # | $T_{1/2}$ (hr) | $T_{max}$ (hr) | $C_{max}$ (ng/mL) | $AUC_{last}$ (ng · hr/mL) | $AUC_{INF\_obs}$ (ng · hr/mL) | $AUC_{INF\_D\_obs}$ (hr · kg/mL) | AUC_% Extrap_obs | $MRT_{last}$ (hr) |
|---|---|---|---|---|---|---|---|---|
| 1001 | 189.77 | 336 | 41 | 12647 | 13890 | 0.0009 | 8.95 | 309.00 |
| 1002 | 263.87 | 528 | 22.4 | 8529 | 13287 | 0.0009 | 35.81 | 399.13 |
| 1003 | 172.95 | 264 | 22.6 | 7783 | 8854 | 0.0006 | 12.09 | 292.05 |
| 1004 | 75.83 | 264 | 101 | 15664 | 15862 | 0.0010 | 1.25 | 275.76 |
| Average | 175.61 | 348.00 | 47 | 11156 | 12974 | 0.0008 | 14.52 | 318.98 |
| Std Dev | 77.36 | 124.71 | 37 | 3689 | 2958 | 0.0002 | 14.90 | 55.13 |

Group 2 (TA-3-039-6):

| Animal # | $T_{1/2}$ (hr) | $T_{max}$ (hr) | $C_{max}$ (ng/mL) | $AUC_{last}$ (ng · hr/mL) | $AUC_{INF\_obs}$ (ng · hr/mL) | $AUC_{INF\_D\_obs}$ (hr · kg/mL) | AUC_% Extrap_obs | $MRT_{last}$ (hr) |
|---|---|---|---|---|---|---|---|---|
| 2001 | 71.52 | 384 | 24.3 | 4829 | 5009 | 0.0003 | 3.60 | 360.01 |
| 2002 | NC | 600 | 5.58 | 1130 | NC | NC | NC | 377.61 |
| 2003 | NC | 648 | 7 | 1759 | NC | NC | NC | 404.67 |
| 2004 | 471.66 | 216 | 3.03 | 1233 | 2104 | 0.0001 | 41.41 | 320.92 |
| Average | 271.59 | 462.00 | 10 | 2238 | 3556 | 0.0002 | 22.51 | 365.80 |
| Std Dev | 282.94 | 200.20 | 10 | 1749 | 2055 | 0.0001 | 26.73 | 35.11 |

Note
that the perceived outlier plasma level of 300 ng/mL at hour 360 was NOT included in the WinNonlin analysis for animal 2001.

Figure 2:
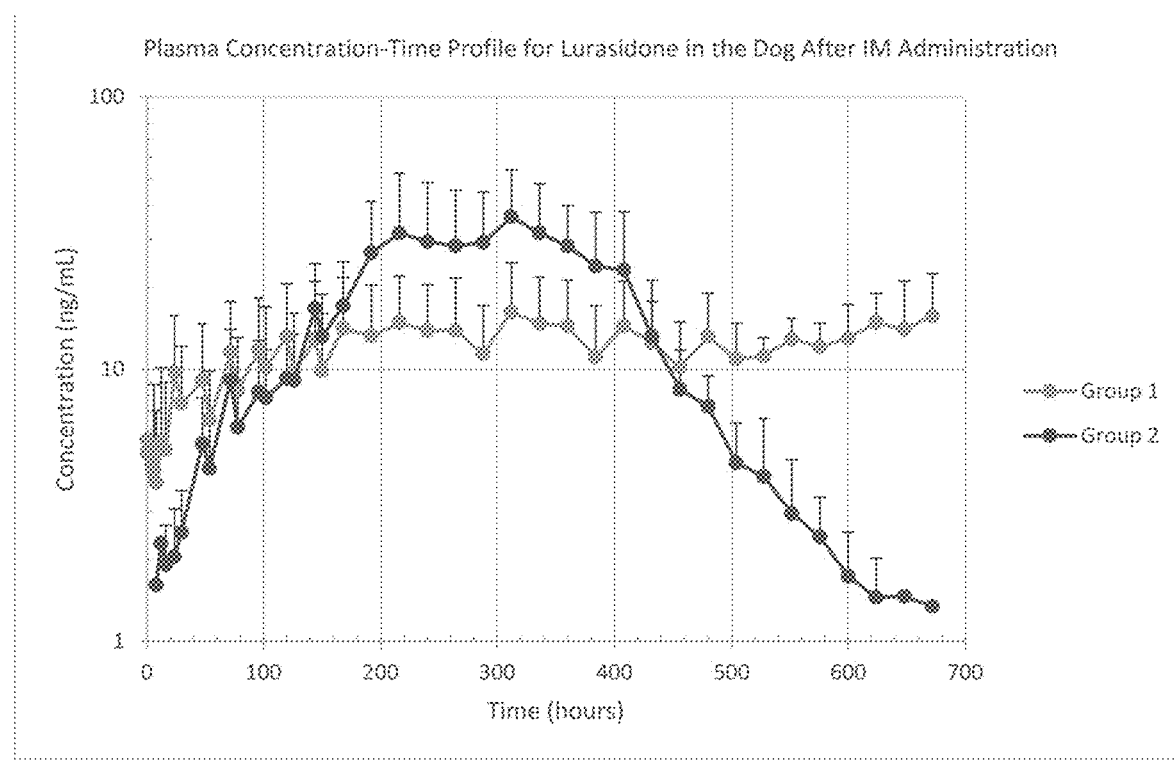
FIG. 2 shows the plasma concentration-time profile from another pharmacokinetic study of lurasidone in dogs.

Results of Study 2 are shown below and in FIG. 2.

Group 1 (TA-3-144):

| Animal # | $T_{1/2}$ (hr) | $T_{max}$ (hr) | $C_{max}$ (ng/mL) | $AUC_{last}$ (ng · hr/mL) | $AUC_{INF\_obs}$ (ng · hr/mL) | $AUC_{INF\_D\_obs}$ (hr · kg/mL) | AUC_% Extrap_obs | $MRT_{last}$ (hr) |
|---|---|---|---|---|---|---|---|---|
| 1001 | NC | 672 | 23.9 | 4707 | NC | NC | NC | 477 |
| 1002 | NC | 480 | 18.8 | 9406 | NC | NC | NC | 355 |
| 1003 | 196 | 312 | 24.6 | 10925 | 13595 | 8.83E−04 | 19.6 | 320 |
| 1004 | 623[a] | 144 | 21.1 | 8019 | 17822[a] | 1.16E−03[a] | 55.0[a] | 329 |
| Average | 196 | 402 | 22.1 | 8264 | 13595 | 8.83E−04 | 19.6 | 370 |
| Std Dev | ND | 226 | 2.67 | 2652 | ND | ND | ND | 72.9 |

Group 1 (TA-3-145):

| Animal # | $T_{1/2}$ (hr) | $T_{max}$ (hr) | $C_{max}$ (ng/mL) | $AUC_{last}$ (ng · hr/mL) | $AUC_{INF\_obs}$ (ng · hr/mL) | $AUC_{INF\_D\_obs}$ (hr · kg/mL) | AUC_% Extrap_obs | $MRT_{last}$ (hr) |
|---|---|---|---|---|---|---|---|---|
| 2001 | 28.6 | 384 | 41.5 | 6865 | 6919 | 4.49E−04 | 0.776 | 342 |
| 2002 | 58.9 | 336 | 54.1 | 13048 | 13163 | 8.55E−04 | 0.872 | 294 |
| 2003 | 65.6 | 312 | 56.7 | 11041 | 11240 | 7.30E−04 | 1.78 | 265 |
| 2004 | 51.9 | 192 | 26.0 | 7117 | 7209 | 4.68E−04 | 1.28 | 273 |
| Average | 51.2 | 306 | 44.6 | 9518 | 9633 | 6.25E−04 | 1.18 | 293 |
| Std Dev | 16.1 | 81.7 | 14.1 | 3032 | 3071 | 1.99E−04 | 0.46 | 34.5 |

[a]Parameters not included in average or standard deviation because of poor data fit (r squared < 0.9)
NC = Parameters not calculable because the data could not be fit
ND = Not Determined because data was insufficient

Example 8

Although combination formulations; both resuspending agent and surfactant in a formulation have remarkable syringeabilities and both particle size distributions and chemical properties of them are stable, their resuspending times can vary. An ideal suspension should possess a short and stable resuspending time by hand-shaking.

In order to evaluate the effect of different percentages of surfactant on resuspending times, we prepared formulations with four suspending agents and increased amount of polysorbate 20 from 0.2% to 1.8%. The formulations were prepared by wet-milling and wet-sieving in medium composed of 0.6% sodium dihydrogen phosphate monohydrate and 0.112% sodium hydroxide aqueous solution. Final suspensions were prepared with active pharmaceutical ingredient concentrations around 400 mg/mL and mean particle sizes close to 20 μm and incorporated suspending agent polyvinyl pyrrolidone K17, carboxymethylcellulose sodium, methylcellulose or polyethylene glycol 4000. The suspensions stood for one month for complete sedimentation of particles, and resuspending times by vertical hand-shaking was determined. Results are shown in Table 6. Each formulations' resuspending time was monitored from initial up to two months were monitored monthly. Results are shown in Table 7.

TABLE 6

| Suspending Agent & Percentage | Polysorbate 20 Percentage (%) | | |
|---|---|---|---|
| | 0.2 | 1 | 1.8 |
| polyvinyl pyrrolidone K17, 0.7% | 20" | 35" | 30" |
| carboxymethylcellulose sodium, 0.1% | 60" | 40" | 45" |
| methylcellulose, 0.1% | 125" | 40" | 40" |
| polyethylene glycol 4000, 5% | 20" | 15" | 15" |

The results show that when polysorbate 20 was only 0.2%, resuspending times varied considerably, and were considerably lengthened when the suspending agent was carboxymethylcellulose sodium or methylcellulose. However, resuspending times became notably shorter and more stable when polysorbate 20 was increased to 1%. Further increasing the polysorbate 20 to 1.8% did not significantly improve resuspension time as compared to formulations with 1% polysorbate 20.

TABLE 7

| Polysorbate 20 Percentage (%) | 0.2 | | | | |
|---|---|---|---|---|---|
| Storage Condition | Initial | RT, 1M | 40° C./75% RH, 1M | RT, 2M | 40° C./75% RH, 2M |
| Suspending Agent & Percentage | | | | | |
| polyvinyl pyrrolidone K17, 0.7% | 30" | 20" | 25" | 20" | |
| carboxymethylcellulose sodium, 0.1% | 30" | 60" | 180" | 50" | >2' |
| methylcellulose, 0.1% | 35" | 125" | 60" | >2' | 30" |
| polyethylene glycol 4000, 5% | 20" | 20" | 40" | 20" | 40" |
| Polysorbate 20 Percentage (%) | 1 | | | | |
| Storage Condition | Initial | RT, 1M | 40° C./75% RH, 1M | RT, 2M | 40° C./75% RH, 2M |
| Suspending Agent & Percentage | | | | | |
| polyvinyl pyrrolidone K17, 0.7% | 25" | 35" | >2' | | 30" |
| carboxymethylcellulose sodium, 0.1% | 25" | 40" | 35" | 35" | 35" |
| methylcellulose, 0.1% | 45" | 40" | 25" | 40" | 50" |
| polyethylene glycol 4000, 5% | 25" | 15" | 20" | 20" | 25" |
| Polysorbate 20 Percentage (%) | 1.8 | | | | |
| Storage Condition | Initial | RT, 1M | 40° C./75% RH, 1M | RT, 2M | 40° C./75% RH, 2M |
| Suspending Agent & Percentage | | | | | |

TABLE 7-continued

| | | |
|---|---|---|
| polyvinyl pyrrolidone K17, 0.7% | 20" | 20" |
| carboxymethycellulose sodium, 0.1% | 45" | |
| methylcellulose, 0.1% | 40" | |
| polyethylene glycol 4000, 5% | 15" | |

Example 9

Four surfactants, i.e., polysorbate 20, polysorbate 80, sorbitan monolaurate 20 and poloxamer 188, were compared and each formulation evaluated for resuspending time (by hand-shaking) and for syringeability after one month. The formulation compositions and results are shown in Table 8, Table 9a and Table 9b.

TABLE 8

Resuspension time of 1-month samples

| | Surfactant & Percentage | | | | | | | |
|---|---|---|---|---|---|---|---|---|
| | Polysorbate 20 | | Polysorbate 80 | | Sorbitan Monolaurate 20 | | Poloxamer 188 | |
| | Mean Particle Size of Drug (μm) | | | | | | | |
| | 19.3 | | 20.5 | | 28.6 | | 19.7 | |
| | Suspending Agent & Percentage | | | | | | | |
| | 0.2% | 1% | 0.2% | 1% | 0.2% | 1% | 0.2% | 1% |
| polyvinyl pyrrolidone K17, 0.7% | 20" | 35" | 20" | 25" | 20" | — | 10" | >2' |
| carboxymethycellulose sodium, 0.1% | 60" | 40" | 30" | 25" | 10" | — | 10" | 1'40" |
| methylcellulose, 0.1% | 125" | 40" | 20" | 25" | 10" | 10" | 20" | 20" |
| polyethylene glycol 4000, 5% | 20" | 15" | 20" | 25" | 25" | 10" | 10" | 1'50" |

The results show that increasing the percentage of polysorbate 20 from 0.2% to 1% PGP maintains resuspension times at the same level or improves them remarkably. When the suspending agent is 0.1% methylcellulose, the resuspension time shortens from 125 seconds to 40 seconds. Both polysorbate 80 and sorbitan monolaurate 20 formulations maintain similar and good resuspension times, at both the 0.2 or 1.0% levels. Most formulations of 1% of poloxamer 188 show significantly longer resuspension times as compared to formulations having 0.2% poloxamer 188.

TABLE 9a

Syringeability of 1-month samples

| | Surfactant & Percentage | | | | | | | |
|---|---|---|---|---|---|---|---|---|
| | Polysorbate 20 | | Polysorbate 80 | | Sorbitan Monolaurate 20 | | Poloxamer 188 | |
| | Mean Particle Size of Drug (μm) | | | | | | | |
| | 19.3 | | 20.5 | | 28.6 | | 19.7 | |
| | Suspending Agent & Percentage | | | | | | | |
| | 0.2% | 1% | 0.2% | 1% | 0.2% | 1% | 0.2% | 1% |
| polyvinyl pyrrolidone K17, 0.7% | 27G | 27G | 27G | 27G | 25G | — | 26G | 27G |
| carboxymethycellulose sodium, 0.1% | 27G | 25G | 27G | 26G | 25G | — | 25G | 27G |
| methylcellulose, 0.1% | 27G | 27G | 25G | 26G | 25G | 27G | 27G | 26G |
| polyethylene glycol 4000, 5% | 26G | 27G | 27G | 27G | 26G | 27G | 27G | 27G |

Syringeability tests were conducted by injecting 1 mL suspensions into pork ham via syringe equipped with gauge 27 needle. If the formulation was not able to pass through 27G needle, then lower gauges were tested until the full sample could pass through the needle into pork ham. The results show that all tested formulations can be injected into pork via needle size of gauge 24 or smaller, which shows that they all have excellent syringeability properties.

TABLE 9b

| | Surfactant & Percentage | | | |
|---|---|---|---|---|
| | Polysorbate 20 | Polysorbate 80 | Sorbitan Monolaurate 20 | Poloxamer 188 |
| | Mean Particle Size of Drug (μm) | | | |
| | 19.3 | 20.5 | 28.6 | 19.7 |
| | Suspending Agent & Percentage | | | |
| | 0.2% | 1% | 0.2% | 1% | 0.2% | 1% | 0.2% | 1% |
| polyethylene glycol 4000, 5% | 26G | 27G | 27G | 27G | 26G | 27G | 27G | 27G |

Syringeability of several formulations with 5% of polyethylene glycol 4000 were tested because these possessed excellent resuspension properties. All tested formulations have outstanding syringeability, passing through gauge 26 at least.

Example 10

Formulations comparing 0.2% and 1% of polysorbate 80 in combination with various suspending agents were tested for resuspension properties. The buffer system is composed of 0.1% sodium dihydrogen phosphate, 0.26% disodium hydrogen phosphate and 0.7% sodium chloride. The resuspension times at one month are shown in Table 10.

TABLE 10

| | Polysorbate 80 Percentage (%) | |
|---|---|---|
| Suspending Agent & Percentage | 0.2 | 1 |
| control sample (without suspending agent) | 30" | 10" |
| polyvinyl pyrrolidone K17, 0.7% | 1'15" | 30" |
| carboxymethycellulose sodium, 0.1% | 1'25" | 30" |
| methylcellulose, 0.1% | 30" | 1'55" |
| polyethylene glycol 4000, 5% | 15" | 25" |
| polyvinyl alcohol, 1% | 40" | 30" |
| hydroxylpropyl betacyclodextrin, 5% | 35" | 20" |
| gelatin, 0.2% | 35" | 25" |
| sucrose, 5% | 30" | 25" |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A depot formulation of lurasidone comprising crystals of lurasidone or an acid salt thereof and having a mean particle size of about 4 μm to about 100 μm,
   wherein the concentration of lurasidone crystals in the formulation is greater than about 250 mg/mL;
   wherein the formulation comprises a suspending agent comprising PEG 4000 in an amount of about 5% (w/w);
   wherein the formulation comprises a surfactant comprising polysorbate 20 in an amount of from about 1% (w/w) to about 2% (w/w);
   wherein the depot formulation is suitable for injection via a syringe needle having a gauge size of 22 gauge or smaller; and
   wherein, upon administration, the formulation delivers a therapeutic dose of lurasidone for at least about 28 days.

2. The depot formulation of claim 1 wherein the concentration of lurasidone crystals in the formulation is about 280 mg/ml or higher.

3. The depot formulation of claim 1 wherein the concentration of lurasidone crystals in the formulation is about 300 mg/ml or higher.

4. The depot formulation of claim 1, wherein the mean particle size is between about 10 μm and about 40 μm.

5. The depot formulation of claim 1, wherein the depot formulation is suitable for injection via a syringe needle having a gauge size of 24 gauge or smaller.

6. A method of treating a schizophrenia or bipolar depression comprising administering the depot formulation of claim 1 to a patient in need thereof via intramuscular injection.

* * * * *